(12) United States Patent
Dabrowiak et al.

(10) Patent No.: US 12,427,055 B2
(45) Date of Patent: Sep. 30, 2025

(54) PATIENT HEAT EXCHANGE SYSTEM WITH TWO AND ONLY TWO FLUID LOOPS

(71) Applicant: ZOLL Circulation, Inc., San Jose, CA (US)

(72) Inventors: Jeremy Thomas Dabrowiak, Redwood City, CA (US); Craig Wendell Pendry, Milpitas, CA (US); Christoph Matthias Pistor, Santa Cruz, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 833 days.

(21) Appl. No.: 16/695,461

(22) Filed: Nov. 26, 2019

(65) Prior Publication Data

US 2020/0268548 A1    Aug. 27, 2020

Related U.S. Application Data

(63) Continuation of application No. 14/180,719, filed on Feb. 14, 2014, now Pat. No. 10,500,088.

(51) Int. Cl.
*A61F 7/02* (2006.01)
*A61F 7/00* (2006.01)
*F25B 39/02* (2006.01)
*A61F 7/12* (2006.01)

(52) U.S. Cl.
CPC ............ *A61F 7/0085* (2013.01); *F25B 39/02* (2013.01); *A61F 2007/0056* (2013.01); *A61F 7/02* (2013.01); *A61F 2007/126* (2013.01); *A61M 2205/12* (2013.01); *A61M 2205/127* (2013.01); *A61M 2205/366* (2013.01)

(58) Field of Classification Search
CPC .. A61F 7/0085; A61F 7/02; A61F 2007/0056; A61F 2007/126; A61M 2205/12; A61M 2205/127; A61M 2205/366; A61M 5/44; F28D 2021/005
See application file for complete search history.

(56) References Cited

U.S. PATENT DOCUMENTS

| | | |
|---|---|---|
| 1,459,112 A | 6/1923 | Mehl |
| 1,726,761 A | 9/1929 | Palmer |
| 1,857,031 A | 5/1932 | Schaffer |
| 2,223,688 A | 12/1940 | Otoo |

(Continued)

FOREIGN PATENT DOCUMENTS

| | | |
|---|---|---|
| CN | 101090685 | 12/2007 |
| CN | 202942288 | 5/2013 |

(Continued)

OTHER PUBLICATIONS

JP Office Action in Japanese Appln. No. 2019-109357, dated Apr. 5, 2022, 12 pages (with English translation).

(Continued)

*Primary Examiner* — Kaitlyn E Smith
*Assistant Examiner* — Yasamin Ekrami
(74) *Attorney, Agent, or Firm* — ZOLL Circulation, Inc.

(57) ABSTRACT

A heat exchange system for exchanging heat with working fluid from an intravascular heat exchange catheter or an external heat exchange pad includes a working fluid that circulates between the catheter or pad and a fluid cassette, and a refrigerant system that flows against the outer sides of cold plates between which the cassette is disposed.

18 Claims, 7 Drawing Sheets

(56) References Cited

U.S. PATENT DOCUMENTS

| | | |
|---|---|---|
| 2,663,030 A | 12/1953 | Dahlberg |
| 2,673,987 A | 4/1954 | Upshaw |
| 2,987,004 A | 6/1961 | Murray |
| 3,140,716 A | 7/1964 | Harrison |
| 3,225,191 A | 12/1965 | Calhoun |
| 3,228,465 A * | 1/1966 | Vadot .................... B60N 3/12 165/167 |
| 3,369,549 A | 2/1968 | Armao |
| 3,425,419 A | 2/1969 | Dato |
| 3,504,674 A | 4/1970 | Swenson |
| 3,726,269 A | 4/1973 | Webster |
| 3,744,555 A | 7/1973 | Fletcher |
| 3,751,077 A | 8/1973 | Hiszpanski |
| 3,834,396 A | 9/1974 | Foster |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress |
| 4,126,132 A | 11/1978 | Portner |
| 4,153,048 A | 5/1979 | Magrini |
| 4,173,228 A | 11/1979 | Van Steenwyk et al. |
| 4,181,132 A | 1/1980 | Parks |
| 4,181,245 A | 1/1980 | Garrett et al. |
| 4,259,961 A | 4/1981 | Hood |
| 4,298,006 A | 11/1981 | Parks |
| 4,459,468 A | 7/1984 | Bailey |
| 4,532,414 A | 7/1985 | Shah et al. |
| 4,552,516 A | 11/1985 | Stanley |
| 4,554,793 A | 11/1985 | Harding, Jr. |
| 4,558,996 A | 12/1985 | Becker |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,869,250 A | 9/1989 | Bitterly |
| 4,906,237 A | 3/1990 | Johansson et al. |
| 4,925,376 A | 5/1990 | Kahler |
| 4,941,475 A | 7/1990 | Williams et al. |
| 5,080,089 A | 1/1992 | Mason et al. |
| 5,092,841 A | 3/1992 | Spears |
| 5,103,360 A | 4/1992 | Maeda |
| 5,106,360 A | 4/1992 | Ishiwara et al. |
| 5,174,285 A | 12/1992 | Fontenot |
| 5,192,274 A | 3/1993 | Bierman |
| 5,195,965 A | 3/1993 | Shantha |
| 5,211,631 A | 5/1993 | Sheaff |
| 5,263,925 A | 11/1993 | Gilmore et al. |
| 5,269,758 A | 12/1993 | Taheri |
| 5,281,215 A | 1/1994 | Milder |
| 5,304,214 A | 4/1994 | DeFord et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,391,030 A | 2/1995 | Lee |
| 5,403,281 A | 4/1995 | O'Neill et al. |
| 5,433,588 A | 7/1995 | Monk |
| 5,433,740 A | 7/1995 | Yamaguchi |
| 5,437,673 A | 8/1995 | Baust et al. |
| 5,458,639 A | 10/1995 | Tsukashima et al. |
| 5,466,208 A | 11/1995 | Jackson |
| 5,476,368 A | 12/1995 | Rabenau |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,624,392 A | 4/1997 | Saab |
| 5,634,907 A | 6/1997 | Rani et al. |
| 5,676,670 A | 10/1997 | Kim |
| 5,693,344 A | 12/1997 | Knight |
| 5,701,905 A | 12/1997 | Esch |
| 5,706,889 A | 1/1998 | Bach et al. |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,746,585 A | 5/1998 | McDunn |
| 5,759,017 A | 6/1998 | Patton et al. |
| 5,776,079 A | 7/1998 | Cope et al. |
| 5,788,647 A | 8/1998 | Eggers |
| 5,803,324 A | 9/1998 | Silberman |
| 5,837,003 A | 11/1998 | Ginsburg |
| 5,857,843 A | 1/1999 | Leason |
| 5,862,675 A | 1/1999 | Scaringe et al. |
| 5,875,282 A | 2/1999 | Jordan |
| 5,879,329 A | 3/1999 | Ginsburg |
| 5,895,418 A | 4/1999 | Saringer |
| 5,908,407 A | 6/1999 | Frazee et al. |
| 5,957,963 A | 9/1999 | Dobak, III |
| 5,980,561 A | 11/1999 | Kolen et al. |
| 5,989,238 A | 11/1999 | Ginsburg |
| 6,019,783 A | 2/2000 | Philips et al. |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak |
| 6,110,139 A | 8/2000 | Loubser |
| 6,110,168 A | 8/2000 | Ginsburg |
| 6,117,065 A | 9/2000 | Hastings et al. |
| 6,117,105 A | 9/2000 | Bresnaham et al. |
| 6,124,452 A | 9/2000 | Di Magno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,149,806 A | 11/2000 | Baer |
| 6,165,207 A | 12/2000 | Balding |
| 6,188,930 B1 | 2/2001 | Carson et al. |
| 6,197,045 B1 | 3/2001 | Carson et al. |
| 6,224,624 B1 | 5/2001 | Lasheras |
| 6,231,594 B1 | 5/2001 | Dae |
| 6,231,595 B1 | 5/2001 | Dobak |
| 6,235,048 B1 | 5/2001 | Dobak |
| 6,238,428 B1 | 5/2001 | Werneth |
| 6,245,095 B1 | 6/2001 | Dobak |
| 6,251,129 B1 | 6/2001 | Dobak |
| 6,251,130 B1 | 6/2001 | Dobak |
| 6,254,626 B1 | 7/2001 | Dobak |
| 6,261,312 B1 | 7/2001 | Dobak |
| 6,264,679 B1 | 7/2001 | Keller |
| 6,283,940 B1 | 9/2001 | Mulholland |
| 6,287,326 B1 | 9/2001 | Pecor |
| 6,290,717 B1 | 9/2001 | Philips et al. |
| 6,299,599 B1 * | 10/2001 | Pham .................... A61F 7/123 604/113 |
| 6,306,161 B1 | 10/2001 | Ginsburg |
| 6,312,452 B1 | 11/2001 | Dobak |
| 6,325,818 B1 | 12/2001 | Werneth |
| 6,338,727 B1 | 1/2002 | Noda et al. |
| 6,364,899 B1 | 4/2002 | Dobak |
| 6,368,304 B1 | 4/2002 | Aliberto |
| 6,375,674 B1 | 4/2002 | Carson et al. |
| 6,379,378 B1 | 4/2002 | Werneth |
| 6,383,144 B1 | 5/2002 | Mooney et al. |
| 6,383,210 B1 | 5/2002 | Magers |
| 6,393,320 B2 | 5/2002 | Lasersohn |
| 6,405,080 B1 | 6/2002 | Lasersohn |
| 6,409,747 B1 | 6/2002 | Gobin et al. |

(56) References Cited

U.S. PATENT DOCUMENTS

| | | |
|---|---|---|
| 6,416,533 B1 | 7/2002 | Gobin et al. |
| 6,419,643 B1 | 7/2002 | Shimada et al. |
| 6,428,563 B1 | 8/2002 | Keller |
| 6,436,130 B1 | 8/2002 | Philips et al. |
| 6,450,990 B1 | 9/2002 | Walker et al. |
| 6,461,379 B1 | 10/2002 | Carson et al. |
| 6,464,666 B1 | 10/2002 | Augustine et al. |
| 6,464,716 B1 | 10/2002 | Dobak, III et al. |
| 6,527,798 B2 | 3/2003 | Ginsburg et al. |
| 6,530,946 B1 | 3/2003 | Noda et al. |
| 6,535,689 B2 | 3/2003 | Augustine |
| 6,544,282 B1 | 4/2003 | Dae et al. |
| 6,551,309 B1 | 4/2003 | Le Pivert |
| 6,554,791 B1 | 4/2003 | Cartledge et al. |
| 6,582,387 B2 | 6/2003 | Derek |
| 6,605,106 B2 | 8/2003 | Schwartz |
| 6,610,083 B2 | 8/2003 | Keller et al. |
| 6,613,280 B2 | 9/2003 | Myrick |
| 6,620,187 B2 | 9/2003 | Carson et al. |
| 6,620,188 B1 | 9/2003 | Ginsburg et al. |
| 6,620,189 B1 | 9/2003 | Machold |
| 6,622,542 B2 | 9/2003 | Derek |
| 6,624,679 B2 | 9/2003 | Tomaivolo et al. |
| 6,635,076 B1 | 10/2003 | Ginsburg |
| 6,635,079 B2 | 10/2003 | Ginsburg |
| 6,645,232 B2 | 11/2003 | Carson et al. |
| 6,648,905 B2 | 11/2003 | Hoglund |
| 6,660,027 B2 | 12/2003 | Gruszecki |
| 6,669,715 B2 | 12/2003 | Hoglund |
| 6,673,098 B1 | 1/2004 | Machold |
| 6,675,835 B2 | 1/2004 | Gerner |
| 6,679,906 B2 | 1/2004 | Hammack et al. |
| 6,685,731 B2 | 2/2004 | Kushnir et al. |
| 6,685,733 B1 | 2/2004 | Dae et al. |
| 6,692,518 B2 | 2/2004 | Carson et al. |
| 6,695,874 B2 | 2/2004 | Machold et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,733,495 B1 | 5/2004 | Bek |
| 6,740,109 B2 | 5/2004 | Dobak, III |
| 6,743,201 B1 | 6/2004 | Donig et al. |
| 6,764,391 B1 | 7/2004 | Grant |
| 6,799,063 B2 | 9/2004 | Carson et al. |
| 6,799,342 B1 | 10/2004 | Jarmon |
| 6,802,855 B2 | 10/2004 | Ellingboe |
| 6,818,012 B2 | 11/2004 | Ellingboe |
| 6,827,728 B2 | 12/2004 | Ellingboe |
| 6,843,099 B2 | 1/2005 | Derek |
| 6,843,800 B1 | 1/2005 | Dobak, III |
| 6,878,156 B1 * | 4/2005 | Noda ............. A61F 7/0085 607/104 |
| 6,887,263 B2 | 5/2005 | Bleam et al. |
| 6,890,347 B2 | 5/2005 | Machold |
| 6,893,419 B2 | 5/2005 | Noda et al. |
| 6,918,924 B2 | 7/2005 | Lasheras |
| 6,969,399 B2 | 11/2005 | Schock et al. |
| 6,974,435 B2 | 12/2005 | Derek |
| 6,997,942 B2 | 2/2006 | Machold |
| 7,070,612 B1 | 7/2006 | Collins et al. |
| 7,104,769 B2 | 9/2006 | Davis |
| 7,140,850 B2 | 11/2006 | Otis, Jr. |
| 7,175,649 B2 | 2/2007 | Machold |
| 7,181,927 B2 | 2/2007 | Collins |
| 7,211,105 B2 | 5/2007 | Magers |
| 7,211,106 B2 | 5/2007 | Dobak |
| 7,247,165 B2 | 7/2007 | Machold |
| 7,258,662 B2 | 8/2007 | Machold |
| 7,357,786 B1 | 4/2008 | Bakke |
| 7,377,935 B2 | 5/2008 | Schock |
| 7,510,569 B2 | 3/2009 | Dae et al. |
| 7,516,909 B2 | 4/2009 | Kaligain |
| 7,645,127 B2 | 1/2010 | Hagen |
| 7,658,755 B2 | 2/2010 | Machold |
| 7,666,215 B2 | 2/2010 | Callister et al. |
| 7,713,036 B2 | 5/2010 | Kojima |
| 7,820,102 B2 | 10/2010 | Myrick |
| 7,822,485 B2 | 10/2010 | Collins |
| 7,846,193 B2 | 12/2010 | Dae et al. |
| 7,857,781 B2 | 12/2010 | Noda et al. |
| 7,879,077 B2 | 2/2011 | Machold |
| 7,892,269 B2 | 2/2011 | Collins et al. |
| 7,914,564 B2 | 3/2011 | Magers |
| 7,959,657 B1 | 6/2011 | Harsy |
| 7,963,986 B2 | 6/2011 | Machold |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 8,128,384 B2 | 3/2012 | Mou |
| 8,177,824 B2 | 5/2012 | Machold |
| 8,226,605 B2 | 7/2012 | Faries, Jr. et al. |
| 8,246,669 B2 | 8/2012 | Machold |
| 8,272,857 B2 | 9/2012 | Norman et al. |
| 8,366,667 B2 | 2/2013 | Chan |
| 8,551,151 B2 | 10/2013 | Machold |
| 8,740,959 B2 | 6/2014 | Machold |
| 8,784,464 B2 | 7/2014 | Machold |
| 8,888,729 B2 | 11/2014 | Noda |
| 8,968,378 B2 | 3/2015 | Ginsburg |
| 9,056,004 B2 | 6/2015 | Ginsburg |
| 9,345,614 B2 | 5/2016 | Schaefer |
| 9,474,644 B2 | 10/2016 | Dabrowiak |
| 9,492,633 B2 | 11/2016 | Dabrowiak |
| 9,675,756 B2 | 6/2017 | Kamen |
| 9,763,823 B2 | 9/2017 | Voorhees |
| 10,022,265 B2 | 7/2018 | Pamichev |
| 2001/0031946 A1 | 10/2001 | Walker |
| 2001/0047196 A1 | 11/2001 | Ginsburg |
| 2002/0004675 A1 | 1/2002 | Lasheras |
| 2002/0013569 A1 | 1/2002 | Sterman |
| 2002/0022823 A1 | 2/2002 | Luo |
| 2002/0096311 A1 | 7/2002 | Kushnir |
| 2002/0117559 A1 | 8/2002 | Kaligain |
| 2002/0134134 A1 | 9/2002 | Derek |
| 2002/0136662 A1 | 9/2002 | Myrick |
| 2002/0138034 A1 | 9/2002 | Derek |
| 2002/0145525 A1 | 10/2002 | Friedman |
| 2002/0183692 A1 | 12/2002 | Callister |
| 2002/0198579 A1 | 12/2002 | Khanna |
| 2003/0036495 A1 | 2/2003 | Datta |
| 2003/0036496 A1 | 2/2003 | Elsner et al. |
| 2003/0041911 A1 | 3/2003 | Gerner |
| 2003/0062090 A1 | 4/2003 | Secondo |
| 2003/0114795 A1 | 6/2003 | Durward |
| 2003/0135252 A1 | 7/2003 | Machold |
| 2003/0236496 A1 | 12/2003 | Samson et al. |
| 2004/0013566 A1 | 1/2004 | Myrick |
| 2004/0019319 A1 | 1/2004 | Derek |
| 2004/0024437 A1 | 2/2004 | Machold |
| 2004/0026068 A1 | 2/2004 | Schmidt |
| 2004/0089050 A1 | 5/2004 | Derek |
| 2004/0089058 A1 | 5/2004 | De Haan |
| 2004/0102825 A1 | 5/2004 | Daoud |
| 2004/0104018 A1 | 6/2004 | Hughes |
| 2004/0143311 A1 | 7/2004 | Machold |
| 2004/0154374 A1 | 8/2004 | Derek |
| 2004/0171935 A1 | 9/2004 | Van Creveld |
| 2004/0190255 A1 | 9/2004 | Cheon |
| 2004/0199230 A1 | 10/2004 | Yon |
| 2004/0210231 A1 | 10/2004 | Boucher |
| 2004/0267340 A1 | 12/2004 | Cioanta |
| 2005/0065584 A1 | 3/2005 | Schiff |
| 2005/0075705 A1 | 4/2005 | Machold |
| 2005/0137662 A1 | 6/2005 | Morris |
| 2005/0156744 A1 | 7/2005 | Pires |
| 2005/0209658 A1 | 9/2005 | Machold |
| 2006/0030917 A1 | 2/2006 | Eccleston |
| 2006/0064146 A1 | 3/2006 | Collins |
| 2006/0069418 A1 | 3/2006 | Schock |
| 2006/0122673 A1 | 6/2006 | Callister |
| 2006/0210424 A1 | 9/2006 | Mallett |

(56) References Cited

U.S. PATENT DOCUMENTS

| | | |
|---|---|---|
| 2006/0241335 A1 | 10/2006 | Benkowski |
| 2006/0253095 A1 | 11/2006 | Stull |
| 2006/0293734 A1 | 12/2006 | Scott |
| 2007/0007640 A1 | 1/2007 | Harnden |
| 2007/0076401 A1 | 4/2007 | Carrez |
| 2007/0093710 A1 | 4/2007 | Maschke |
| 2007/0156006 A1 | 7/2007 | Smith |
| 2007/0173759 A1* | 7/2007 | Augustine ............ A61M 5/44 604/113 |
| 2007/0191981 A1 | 8/2007 | Machold |
| 2007/0203552 A1 | 8/2007 | Machold |
| 2007/0278155 A1 | 12/2007 | Lo et al. |
| 2007/0293919 A1 | 12/2007 | Machold |
| 2008/0082051 A1 | 4/2008 | Miller |
| 2008/0114430 A1 | 5/2008 | Collins |
| 2008/0119916 A1 | 5/2008 | Choucair |
| 2008/0230530 A1 | 9/2008 | Augustine |
| 2008/0262409 A1 | 10/2008 | Derrico |
| 2008/0267599 A1* | 10/2008 | Arnold ............... A61M 5/36 392/470 |
| 2008/0269663 A1 | 10/2008 | Arnold |
| 2009/0010627 A1* | 1/2009 | Lindsay ............ A61M 1/155 392/470 |
| 2009/0065565 A1 | 3/2009 | Cao |
| 2009/0099518 A1 | 4/2009 | Magers |
| 2009/0247963 A1 | 10/2009 | Bleam |
| 2009/0299287 A1 | 12/2009 | Carson |
| 2010/0036486 A1 | 2/2010 | Mazur |
| 2010/0049119 A1 | 2/2010 | Norman et al. |
| 2010/0082000 A1 | 4/2010 | Honeck |
| 2010/0129248 A1 | 5/2010 | Mou |
| 2010/0204765 A1 | 8/2010 | Hall |
| 2010/0256601 A1 | 10/2010 | Lippert |
| 2011/0022136 A1 | 1/2011 | Scott |
| 2011/0046551 A1 | 2/2011 | Augustine |
| 2011/0137249 A1 | 6/2011 | Collins |
| 2011/0184253 A1 | 7/2011 | Archer |
| 2011/0208276 A1 | 8/2011 | Machold |
| 2011/0208277 A1 | 8/2011 | Machold |
| 2011/0208278 A1 | 8/2011 | Machold |
| 2011/0213305 A1 | 9/2011 | Jonsson |
| 2012/0095536 A1 | 4/2012 | Machold |
| 2012/0100023 A1 | 4/2012 | Hanazuka |
| 2012/0158103 A1* | 6/2012 | Bledsoe ............. A61F 7/02 607/104 |
| 2012/0226338 A1 | 9/2012 | Machold |
| 2013/0071270 A1 | 3/2013 | Zupp |
| 2013/0079855 A1 | 3/2013 | Helkowski |
| 2013/0079856 A1 | 3/2013 | Dabrowiak |
| 2013/0090708 A1 | 4/2013 | Dabrowiak |
| 2013/0090709 A1 | 4/2013 | Machold |
| 2013/0098880 A1 | 4/2013 | Korolev |
| 2013/0150929 A1 | 6/2013 | Machold |
| 2013/0150930 A1 | 6/2013 | Machold |
| 2013/0172805 A1 | 7/2013 | Truckai |
| 2013/0178923 A1 | 7/2013 | Dabrowiak |
| 2013/0331774 A1 | 12/2013 | Farrell |
| 2013/0337732 A1 | 12/2013 | Nilliams |
| 2014/0081202 A1 | 3/2014 | Tsoukalis |
| 2014/0094880 A1 | 4/2014 | Lim |
| 2014/0094882 A1 | 4/2014 | Lim |
| 2014/0094883 A1 | 4/2014 | Lim |
| 2014/0276792 A1 | 9/2014 | Kaveckis |
| 2014/0277302 A1 | 9/2014 | Weber |
| 2014/0364928 A1 | 12/2014 | Machold |
| 2015/0223974 A1 | 8/2015 | Dabrowiak |
| 2015/0230973 A1 | 8/2015 | Dabrowiak |
| 2015/0230974 A1 | 8/2015 | Pistor |
| 2015/0230975 A1 | 8/2015 | Dabrowiak |
| 2015/0314055 A1 | 11/2015 | Hogard |
| 2016/0022477 A1 | 1/2016 | Schaefer |
| 2016/0089184 A1 | 3/2016 | Truckai |
| 2016/0166758 A1 | 6/2016 | Norman et al. |
| 2016/0228291 A1 | 8/2016 | Callister |
| 2016/0287432 A1 | 10/2016 | Dabrowiak |
| 2016/0287433 A1 | 10/2016 | Mazzone |
| 2016/0287434 A1 | 10/2016 | Dabrowiak |
| 2016/0287435 A1 | 10/2016 | Pamichev |
| 2017/0035604 A1 | 2/2017 | Dabrowiak |
| 2018/0185192 A1 | 7/2018 | Mazzone |
| 2018/0185193 A1 | 7/2018 | Mazzone |
| 2018/0207024 A1 | 7/2018 | Dabrowiak |
| 2018/0214302 A1 | 8/2018 | Dabrowiak |
| 2018/0214303 A1 | 8/2018 | Dabrowiak |
| 2018/0311072 A1 | 11/2018 | Pamichev |
| 2018/0325725 A1 | 11/2018 | Dabrowiak |
| 2019/0133820 A1 | 5/2019 | Jacobsen |

FOREIGN PATENT DOCUMENTS

| | | |
|---|---|---|
| DE | 19531935 | 2/1997 |
| EP | 0663529 | 5/1997 |
| GB | 2040169 | 8/1980 |
| GB | 1183185 | 2/1985 |
| GB | 2212262 | 7/1989 |
| GB | 2383828 | 7/2003 |
| JP | S 60-256773 A | 12/1985 |
| JP | S61100243 | 5/1986 |
| JP | 7308338 | 11/1995 |
| JP | 09-215754 | 8/1997 |
| JP | 10-0127777 | 5/1998 |
| JP | 10-305103 | 11/1998 |
| JP | 2001147095 | 5/2001 |
| JP | 2002534160 | 10/2002 |
| JP | 2003028582 | 1/2003 |
| JP | 2003508150 | 3/2003 |
| JP | 2003-194425 A | 7/2003 |
| JP | 2003524507 | 8/2003 |
| JP | 2008154751 | 7/2008 |
| JP | 2008531114 | 8/2008 |
| JP | 2008539034 | 11/2008 |
| JP | 2009500066 | 1/2009 |
| JP | 2011505929 | 3/2011 |
| JP | 2011137621 | 7/2011 |
| JP | 2011182849 | 9/2011 |
| JP | 2014023604 | 2/2014 |
| JP | 2017508509 | 3/2017 |
| JP | 2017511716 | 4/2017 |
| WO | WO 1990001682 | 2/1990 |
| WO | WO 1993002730 | 2/1993 |
| WO | WO 1993004727 | 3/1993 |
| WO | WO 1994000177 | 1/1994 |
| WO | WO 1995003680 | 2/1995 |
| WO | WO 1994001177 | 1/1997 |
| WO | WO 1997025011 | 7/1997 |
| WO | WO 1998024491 | 6/1998 |
| WO | WO 1998040017 | 9/1998 |
| WO | WO 2000010494 | 3/2000 |
| WO | WO 2001013809 | 3/2001 |
| WO | WO 2001026719 | 4/2001 |
| WO | WO 2001064146 | 9/2001 |
| WO | WO 2001076517 | 10/2001 |
| WO | WO 2001083001 | 11/2001 |
| WO | WO 2015119671 | 8/2005 |
| WO | WO 2005117546 | 12/2005 |
| WO | WO 2006036585 | 4/2006 |
| WO | WO 2009056640 | 5/2009 |
| WO | WO 2010040819 | 4/2010 |
| WO | WO 2012175089 | 12/2012 |
| WO | WO 2014160422 | 10/2014 |
| WO | WO 2015119670 | 8/2015 |
| WO | WO 2015122938 | 8/2015 |

OTHER PUBLICATIONS

American Urethane Inc., "Polyurethane Properties", available Oct. 12, 2010, http://web.archive.org/web/20101012211957/ hllp://americanurethane.com/polyurethane-properties.html.

Baharlou, "Written Opinion of the International Searching Authority", mailed Oct. 12, 2017, from Counterpart PCT application PCT/US2016/024970.

(56) References Cited

OTHER PUBLICATIONS

Behringer et al., "Rapid Hypothermic Aortic Flush Can Achieve Survival without Brain Damage after 30 Minutes Cardiac Arrest in Dogs", anesthesiology, V. 93, No. 6, 1491-1499, Dec. 2000.

Bontke, "Die Regelung der Warmebildung bei kunstlicher Hypothermie", PFFugers Archiv, Bd. 266, S. 408-421 (1958).

Bontke, "Intravasale Kuhlung", Pffugers Archiv, Bd. 263, S. 145-165 (1956).

Chinese Office Action in Application No. 201480077207.7, dated Jul. 3, 2019, 24 pages.

Dabrowiak "Heat Exchange System for Patient Temperature Control with Multiple Coolant Chambers for Multiple Heat Exchange Modalities", related pending U.S. Appl. No. 14/175,545 non-final office action dated Feb. 12, 2016 (1156-117).

Dabrowiak et al., "Fluid Cassette with Tensioned Polymeric Membranes for Patient Heat Exchange System", related pending U.S. Appl. No. 14/180,613, applicant's response to non-final office action filed Jun. 1, 2016.

Dabrowiak et al., "Heat Exchange System for Patient Temperature Control with Multiple Coolant Chambers for Multiple Heat Exchange Modalities" file history of related U.S. Appl. No. 14/175,545, filed Feb. 7, 2014. (1156.117).

Dabrowiak et al., "Patient Heat Exchange System with Transparent Wall for Viewing Circulating Refrigerant" file history of related U.S. Appl. No. 14/276,202, filed May 13, 2014. (1156-117.CIP).

Dabrowiak et al., "Patient Heat Exchange System with Transparent Wall for Viewing Circulating Refrigerant", related pending U.S. Appl. No. 14/276,202, applicant's response to non-final office action filed Jun. 1, 2016 (1156-117.CIP).

Dabrowiak et al., "Cold Plate Design in Heat Exchanger for Intravascular Temperature Management Catheter and/or Heat Exchange Pad", filed history of related U.S. Appl. No. 14/675,504, filed Mar. 31, 2015.

Dabrowiak et al., "Fluid Cassette with Tensioned Polymeric Membranes for Patient Heat Exchange System" file history of related U.S. Appl. No. 14/180,613, filed Feb. 14, 2014. (1156.114).

Dabrowiak et al., "Fluid Cassette with Tensioned Polymeric Membranes for Patient Heat Exchange System" file history of related pending U.S. Appl. No. 14/180,655 applicant's response to non-final office action filed Jun. 1, 2016 (1156-115).

Dabrowiak et al., "Fluid Cassette with Tensioned Polymeric Membranes for Patient Heat Exchange System" related pending U.S. Appl. No. 14/180,613, non-final office action dated May 19, 2016 (1156-114).

Dabrowiak et al., "Fluid Cassette with Tensioned Polymeric Membranes for Patient Heat Exchange System", related pending U.S. Appl. No. 14/180,613 final office action dated Jul. 15, 2016 (1156-114).

Dabrowiak et al., "Fluid Cassette with Tensioned Polymeric Membranes for Patient Heat Exchange System", related pending U.S. Appl. No. 14/180,613, applicant's response to non-final office action filed Jun. 1, 2016 (1156-114).

Dabrowiak et al., "Patient Heat Exchange System with Transparent Wall for Viewing Circulating Refrigerant" file history of related U.S. Appl. No. 14/275,202, filed May 13, 2014 (1156-117.CIP).

Dabrowiak et al., "Patient Heat Exchange System with Transparent Wall for Viewing Circulating Refrigerant", related pending U.S. Appl. No. 14/276,202 final office action dated Jul. 15, 2016.

Dabrowiak et al., "Patient Heat Exchange System with Transparent Wall for Viewing Circulating Refrigerant", related pending U.S. Appl. No. 14/276,202, non-final office action dated May 19, 2016 (1156-117.CIP).

Dabrowiak et al., "Patient Heat Exchange System with Transparent Wall for Viewing Circulating Refrigerant", related pending U.S. Appl. No. 14/276,202, applicant's response to non-final office action dated Jun. 1, 2016 (1156-117.CIP).

Dabrowiak et al., "Patient Heat Exchange System with Transparent Wall for Viewing Circulation Refrigerant", related pending U.S. Appl. No. 14/276,202, applicant's response to non-final office action filed Aug. 21, 2018. (1156-117.CIP).

Dabrowiak et al., "Patient Heat Exchange System With Two and Only Two Fluid Loops", file history of related U.S. Appl. No. 14/180,719, filed Feb. 14, 2014 (1156.116).

Dabrowiak et al., "Patient Heat Exchange System with Two and Only Two Fluid Loops", related U.S. Appl. No. 14/180,719, Non-Final Office Action dated Jun. 7, 2016. (1156-116).

Dabrowiak et al., "Patient Heat Exchange System with Two and Only Two Fluid Loops", related U.S. Appl. No. 14/180,719, Applicant's response to the Non-Final Office Action dated Sep. 7, 2016 (1156-116).

Dabrowiak et al., "Patient Heat Exchanger System with Transparent Wall for Viewing Circulation Refrigerant", related pending U.S. Appl. No. 14/276,202, non-final office action dated Feb. 21, 2018. (1156-117.CIP).

Dabrowiak et al., "Patient Heat Exchange System with Two and Only Two Fluid Loops", related U.S. Appl. No. 14/180,719, Applicant's Response to the Non-Final Office Action filed Sep. 7, 2016. (1156-116).

Dabrowiak, "Heat Exchange System for Patient Temperature Control With Multiple Coolant Chambers For Multiple Heat Exchange Modalities", File History of related pending U.S. Appl. No. 15/332,519, filed Oct. 24, 2016. (1156-117.CON).

Dabrowiak, "Heat Exchange System for Patient Temperature Control with Multiple Coolant Chambers for Multiple Heat Exchange Modalities", file history of related U.S. Appl. No. 14/175,545, filed Feb. 7, 2014 (1156.117).

Dabrowiak, "Heat Exchange System for Patient Temperature Control with Multiple Coolant Chambers for Multiple Heat Exchange Modalities", related pending U.S. Appl. No. 14/175,545 applicants response to non-final office action dated May 2, 2016 (1156-117).

Dabrowiak, "Serpentine Heat Exchange Assembly for Removable Engagement with Patient Heat Exchange System" file history of related U.S. Appl. No. 14/675,421, filed Mar. 31, 2015.

Dabrowiak, "Working fluid cassette with hinged plenum or enclosure for interfacing heat exchanger with intravascular temperature management catheter", filed history of related U.S. Appl. No. 14/676,672, filed Apr. 1, 2015.

European Office Action in Application No. 16775853.1, dated Nov. 6, 2019, 5 pages.

Extra Packaging Corp, Polyurethane Prosperities and Characteristics, accessed May 9, 2016 at http://www.extrapackaging.com/polyurethane/properites.php.

Hendricks et al., "Heat Exchange System for Patient Temperature Control with Easy Loading High Performance Peristaltic Pump" file history of related U.S. Appl. No. 14/534,718, filed Nov. 6, 2014. (1156.120).

Hendricks et al., "Heat Exchange System for Patient Temperature Control with Easy Loading High Performance Peristaltic Pump", related U.S. Appl. No. 14/534,718, Non-Final Office Action dated Jul. 25, 2016. (1156-120).

International Search Report dated Jun. 25, 2018 in related PCT Application No. PCT/US2018/016752, 4 pages.

International Search Report dated Jun. 25, 2018 in related PCT Application No. PCT/US2018/016754, 4 pages.

Japanese Office Action in Application No. 2017-549496, dated Mar. 10, 2020, 4 pages.

Japanese Office Action in Application No. 2018-118084, dated Sep. 2, 2019, 10 pages.

Japanese Office Action in Application No. 2018-160938, dated Jul. 19, 2019, 6 pages.

Mazzone, "Proximal Mounting of Temperature Sensor in Intravascular Temperature Management Catheter", file history of related U.S. Appl. No. 14/675,452, filed Mar. 31, 2015 (1156.156).

Pamichev et al., "Heat Exchange System for Patient Temperature Control With Easy Loading High Performance Peristatic Pump", file history of related U.S. Appl. No. 14/676,682, filed Apr. 1, 2015 (1165.159).

Pamichev et al., "Heat exchange system for patient temperature control with easy loading high performance penstatic pump", filed history of related application serial No. 14/676/682, filed Apr. 1, 2015 (1156.158).

(56) References Cited

OTHER PUBLICATIONS

Pistor et al., "Fluid Cassette with Polymeric Membranes and Integral Inlet and Outlet Tubes for Patient Heat Exchange System" file history of related U.S. Appl. No. 14/180,655, filed Feb. 14, 2014. (1156.115).

Pistor et al., "Fluid Cassette with Polymeric Membranes and Integral Inlet and Outlet Tubes for Patient Heat Exchange System", related pending U.S. Appl. No. 14/180,655, applicant's response to non-final office action file Jun. 1, 2016 (1156-115).

Pistor et al., "Fluid Cassette With Polymeric Membranes and Integral Inlet and Outlet Tubes for Patient Heat Exchange System", related U.S. Appl. No. 14/180,655, Final Office dated Sep. 8, 2016. (1156-115).

Pistor et al., "Fluid Cassette with Polymeric Membranes and Integral Intel and Outlet Tubes for Patient Heat Exchange System", related pending U.S. Appl. No. 14/180,655, non-final office action dated May 18, 2016 (1156-115).

Watts et al., "Hypothermic Coagulopathy in trauma: Effect of Varying levels of Hypothermia on Enzyme Speed, Platelet Function, and Fibrinolytic Activity" The Journal of Trauma: Injury, Infection, and Critical Care, Vo. 44, No. 5, 848-854, 1998.

Wittman-Regis, "Written Opinion of the International Searching Authority", dated Oct. 12, 2017, from counterpart PCT application PCT/US2016/025030.

\* cited by examiner

PATIENT HEAT EXCHANGE SYSTEM WITH TWO AND ONLY TWO FLUID LOOPS

CLAIM OF PRIORITY

This patent application is a continuation of U.S. patent application Ser. No. 14/180,719, filed on Feb. 14, 2014, the disclosures of which are incorporated herein by reference.

I. FIELD OF THE INVENTION

The present application relates generally to patient heat exchange systems with two and only two fluid loops.

II. BACKGROUND OF THE INVENTION

Patient temperature control systems have been introduced to prevent fever in patients in the neuro ICU due to suffering from sub-arachnoid hemorrhage or other neurologic malady such as stroke. Also, such systems have been used to induce mild or moderate hypothermia to improve the outcomes of patients suffering from such maladies as stroke, cardiac arrest, myocardial infarction, traumatic brain injury, and high intracranial pressure. Examples of intravascular heat exchange catheters are disclosed in U.S. Pat. Nos. 6,419, 643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, all of which are incorporated herein by reference.

External patient temperature control systems may be used. Such systems are disclosed in U.S. Pat. Nos. 6,827, 728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference.

SUMMARY OF THE INVENTION

A heat exchange system for exchanging heat with working fluid from an intravascular heat exchange catheter or an external heat exchange pad includes a working fluid circuit configured for circulating working fluid between a fluid cassette and the catheter or pad. The system also includes a refrigerant circuit configured for circulating refrigerant between a compressor and sides of cold plates between which the cassette is disposable.

In example embodiments a cassette slot is defined between the cold plates for receiving the fluid cassette. A distance between the cold plates (e.g., the width of the slot) can be less than forty mils (0.040") and may be between twenty nine mils and thirty one mils (0.029"-0.031"). The cold plates can be nearly square and can abut each other along left and right side walls. In examples, respective vertically elongated cassette frame receptacles are located immediately inboard of the respective side walls with the slot extending between the side walls and terminating at the receptacles, and the frame receptacles are wider than the slot. At least one cold plate may be formed with a serpentine passageway through which the refrigerant flows.

In another aspect, a system includes two heat transfer plates parallel to each other and defining a slot between them configured for receiving a working fluid cassette through which working fluid flows to and from an intravascular catheter in a working fluid circuit. A refrigerant circuit supplies refrigerant to at least one of the plates to exchange heat therewith. The refrigerant circuit includes a compressor and is the only fluid circuit in thermal contact with the working fluid circuit other than a bloodstream of a patient in which the catheter can be positioned.

In another aspect, a method includes circulating refrigerant between a compressor and a cold plate, and circulating working fluid between an intravascular heat exchange catheter and a fluid cassette disposed on contact with the cold plate to exchange heat between the refrigerant and the working fluid through the cold plate.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
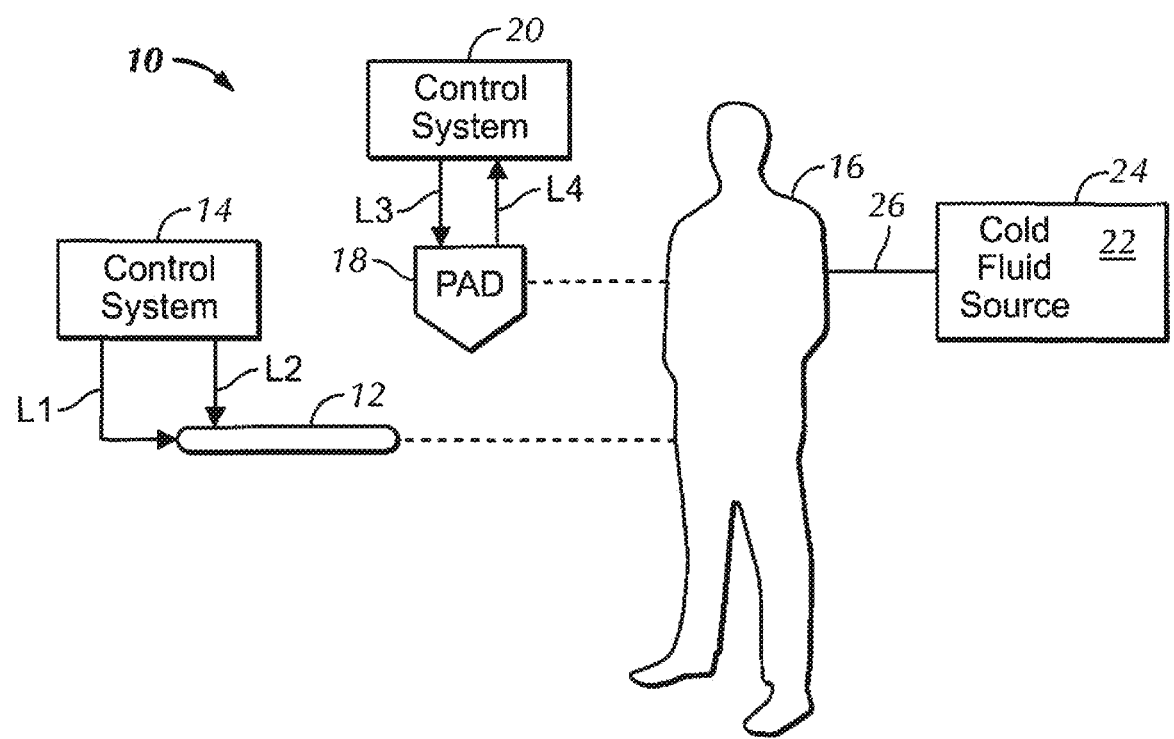
FIG. 1 is a schematic view of a non-limiting system in accordance with the present invention.

Referring initially to FIG. 1, in accordance with present principles, a system 10 may include an intravascular heat exchange catheter 12 controlled by a control system 14 to induce control patient temperature, e.g., to prevent the patient 16 from becoming febrile or to induce therapeutic hypothermia in the patient 16. In the catheter, working fluid (also referred to as "coolant") such as but not limited to saline circulates (typically under the influence of a pump in the controller) in a closed loop from the control system 14, through a fluid supply line L1, through the catheter 12, and back to the system 14 through a fluid return line L2, such that no coolant enters the body. While certain preferred catheters are disclosed below, it is to be understood that other catheters can be used in accordance with present principles, including, without limitation, any of the catheters disclosed above or in the following U.S. patents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,254,626, 6,261,312, 6,312,452, 6,325,818, 6,409,747, 6,368,304, 6,338,727, 6,299,599, 6,287,326, 6,126,684. The catheter 12 may be placed in the venous system, e.g., in the superior or inferior vena cava.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents. The temperature of the pad 18 can be controlled by a pad control system 20 in accordance with principles set forth in the external pad patents to exchange heat with the patient 16, including to induce therapeutic mild or moderate hypothermia in the patient in response to the patient presenting with, e.g., cardiac arrest, myocardial infarction, stroke, high intracranial pressure, traumatic brain injury, or other malady the effects of which can be ameliorated by hypothermia. The pad 18 may receive working fluid from the system 20 through a fluid supply line L3, and return working fluid to the system 20 through a fluid return line L4. Note that in some embodiments, the systems 14, 20 are established in a single assembly.

To cool the patient while awaiting engagement of the catheter 12 and/or pad 18 with the patient, cold fluid 22 in a cold fluid source 24 may be injected into the patient and in particular into the patient's venous system through a pathway 26. Without limitation, the pathway 26 may an IV line, the source 24 may be an IV bag, and the fluid 22 may be chilled saline, e.g., saline at the freezing point or slightly warmer. Or, the source may be a syringe, and the saline can be injected directly into the bloodstream of the patient.

Figure 2:
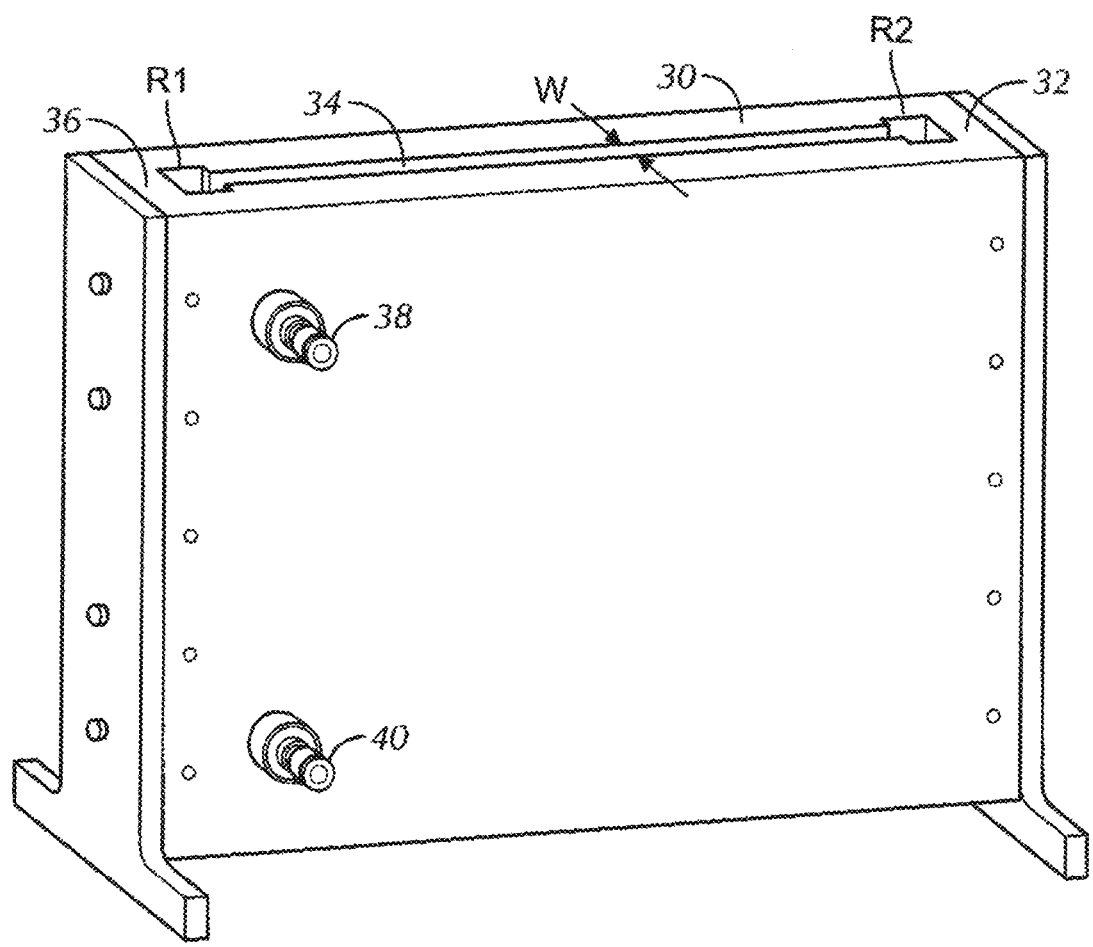
FIG. 2 is a perspective view of an example working fluid cassette holder portion of a heat exchange system.

Now referring to FIG. 2, a portion of either of the heat exchangers in the control systems 14, 20 is shown which includes at least two cold plates 30, 32 defining a cassette slot 34 between them. In one embodiment, the width "W" of the slot 34 is less than forty mils (0.040"), and may be between twenty nine mils and thirty one mils (0.029"-0.031") or may have a nominal slot width of 0.035". In a specific example the width "W" may be thirty mils. In other embodiments, when a disposable heat exchange bag with serpentine channels is used, a larger gap between the cold plates may be used, e.g., 0.060"-0.120" and more preferably 0.080" to promote pumping saline through the bag without excessive backpressure.

The cold plates 30, 32 may be made of metal, and can be rectilinear as shown and indeed may be nearly square. The cold plates 30, 32 may abut each other along left and right side walls 36, with elongated vertical cassette frame receptacles R1 and R2 being located immediately inboard of the respective side walls 36 and with the slot 34 extending between the walls 36 and terminating at the receptacles R1, R2 as shown. The frame receptacles R1, R2 are wider than the slot 36.

In the example shown, refrigerant inlet and outlet tubes 38, 40 extend through at least one of the cold plates 32 to communicate refrigerant from a compressor into a refrigerant passageway in the cold plate. Each cold plate may have its own refrigerant inlet and outlet tubes, or, in the embodiment shown, only one cold plate may be formed with refrigerant inlet and outlet tubes and the other cold plate either thermally coupled to the cold plate in which the refrigerant flows and/or receiving refrigerant from the other cold plate through passageways formed through one or both of the side walls 36.

Figure 3:
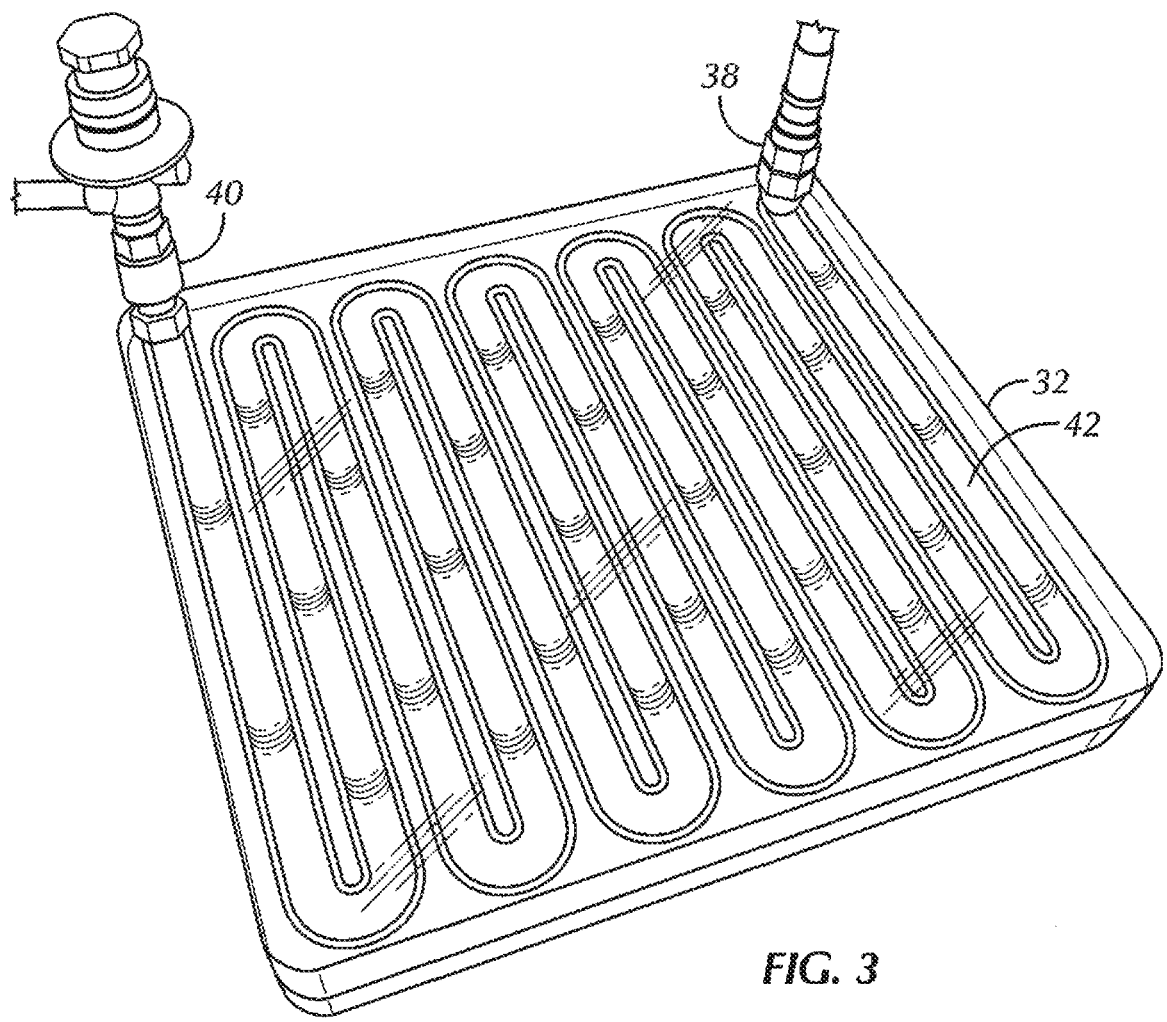
FIG. 3 is a perspective view of one half of the cassette holder shown in FIG. 2, with the opaque metal inner surface shown in transparency to reveal the serpentine refrigerant passageway.

FIG. 3 shows details of an example cold plate 32 looking at the inner surface in transparency, it being understood that the inner surface typically is metal and that the serpentine refrigerant passageway 42 shown in FIG. 3 typically would not be visible to the human eye. In any case, the example refrigerant passageway that fluidly connects the refrigerant inlet 38 to the refrigerant outlet 40 may be serpentine-shaped as shown, or may be some other shape or pattern such as a herringbone pattern a wave pattern, etc. Alternatively, parallel channel passages may be used. For instance, ten one-inch wide channels may be formed in parallel, thereby achieving a 10×10" surface area.

Figure 4:
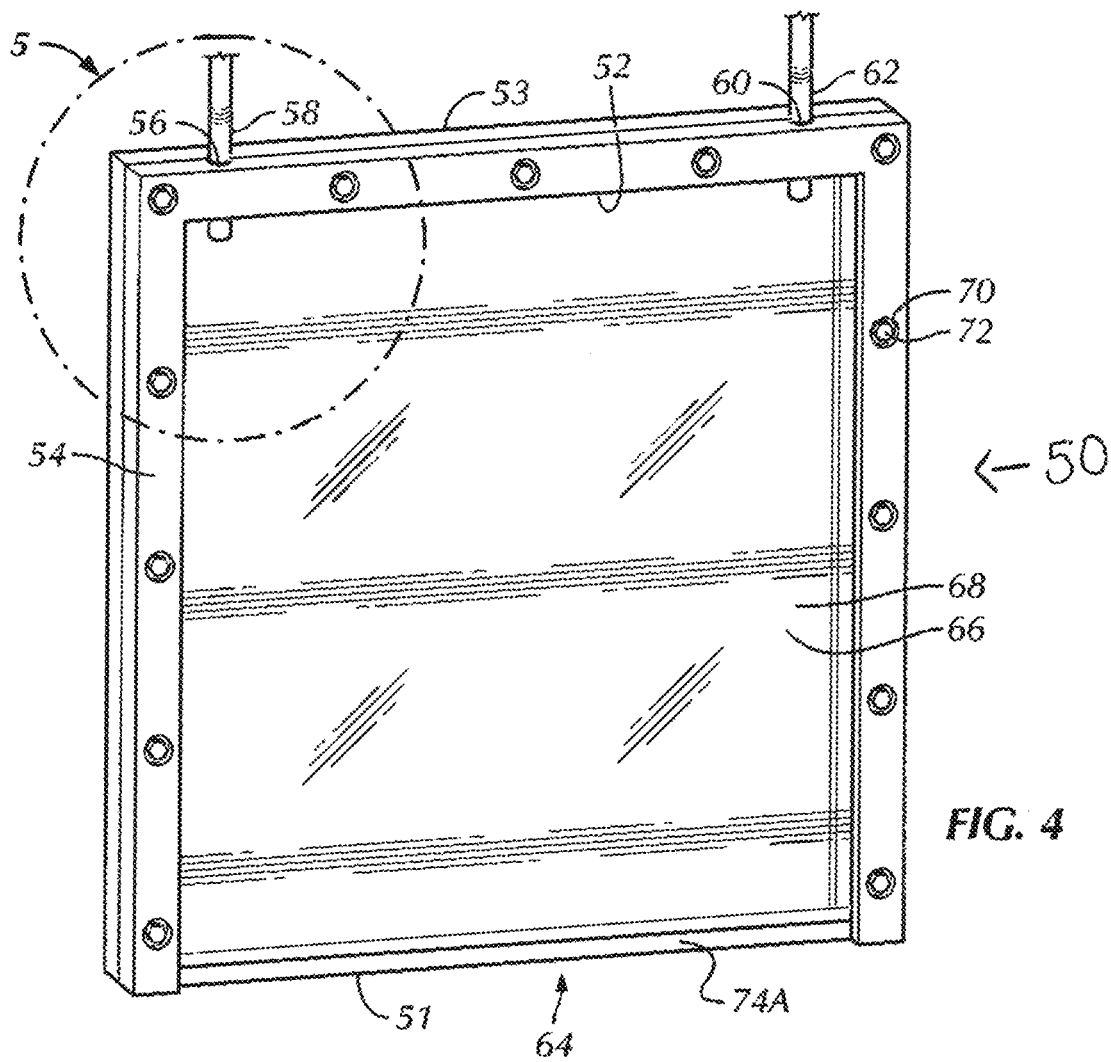
FIG. 4 is a perspective view of an example working fluid cassette configured to engage the cassette holder shown in FIGS. 2 and 3.

FIG. 4 shows an example working fluid cassette 50 according to present principles. The cassette 50 is configured to fit snugly into the slot 34 and cassette frame receptacles R1, R2 defined between the cold plates 30, 32. Working fluid such as saline from a patient-engageable heat exchange member such as the catheter 12 or pad 18 flows through the cassette 50 in operation, with the working fluid exchanging heat with the refrigerant in the cold plates. In example embodiments, the cassette 50 is a low cost single-use disposable item that can contain, e.g., sterile saline which circulates through the catheter 12. The cassette may be placed by a medical caregiver in the slot 34 between the cold plates 30, 32 and the membrane portion which defines a space or working fluid chamber through which the example saline flows inflates when the working fluid flows through it, achieving thermal contact with the cold plates 30, 32.

In the example shown, the cassette 50 includes a frame 52 defining a periphery and a preferably rectilinear opening bounded as shown on at least three sides by the periphery of the frame. In the non-limiting example shown, the frame includes an elongated parallelepiped-shaped top rail 53 and elongated parallelepiped-shaped left and right side rails 54 parallel to each other and perpendicular to the top rail 32. The example frame 52 has no bottom rail opposite the top rail. In any case, the example frame 52 is rectilinear and is configured for being closely received between the two cold plates 30, 32, with the side rails 54 slidably engageable with the frame receptacles R1, R2 between the cold plates 30, 32 and with the below-described membrane assembly passed through the slot 36 to be in close juxtaposition with the refrigerant channels in the cold plates.

Figure 5:
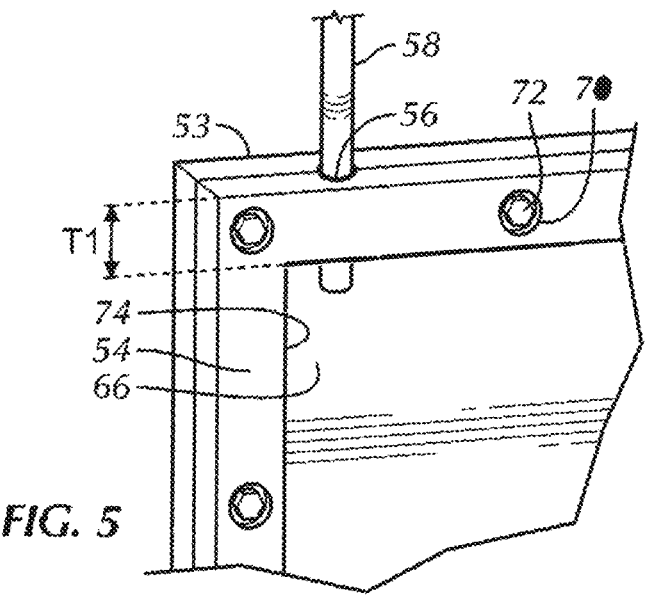
FIG. 5 is a close up perspective view of the cassette shown in FIG. 4, illustrating an inlet tube extending partially down into the stretched membrane chamber, it being understood that an opposed outlet tube may be similarly disposed on the opposite side of the cartridge and that both the inlet and outlet tubes may extend any length down their respective sides in the cassette.
Figure 4A:
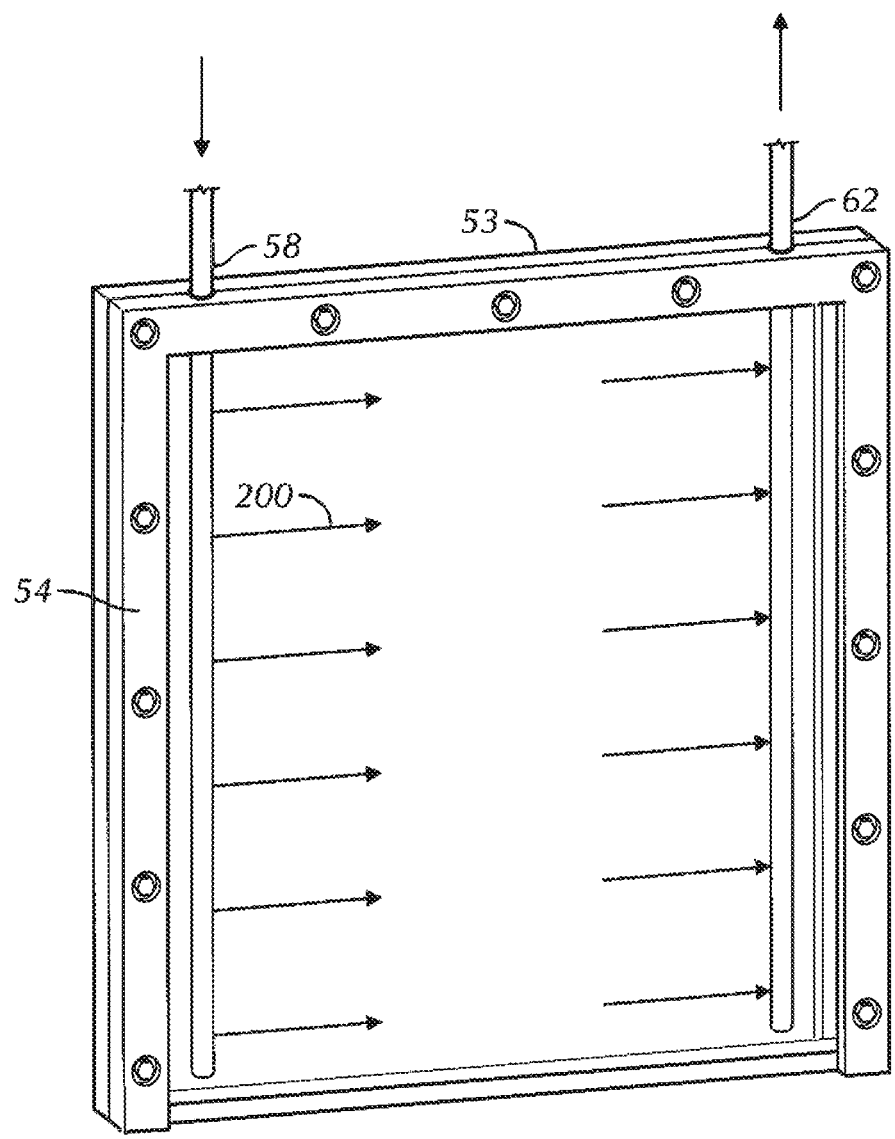
FIG. 4A is similar to FIG. 4, showing the inlet and outlet tubes extending from the top to the bottom of the membrane assembly.

In cross-references to FIGS. 4 and 5, the frame, in the example shown, the top rail 53 thereof, is formed with a fluid inlet 56 in which an inlet tube 58 has been disposed and a fluid outlet 60 in which an outlet tube 62 has been disposed. Both the inlet and outlet establish respective fluid passageways through the frame into the opening. The inlet and outlet tubes 58, 62 may be engaged with the fluid return and supply lines L3, LA that are associated with the catheter 12. The tubes 58, 62 may terminate at just below the top rail 53 (FIG. 4), or they may extend any desired length down to the bottom of the assembly, i.e., the tubes 58, 62 may extend almost the entire length of the left and right side rails 54, ending just above the below-described bottom seam of the membrane assembly (FIG. 4A).

Indeed, a polymeric membrane assembly 64 is connected to the frame 52, blocking the opening that is bounded on three sides by the frame as shown. The membrane assembly includes a first membrane 66 that is parallel to and closely spaced from a second membrane 68, leaving a space there between which establishes a working fluid chamber. The fluid inlet 56 and fluid outlet 60 communicate with the space between the membranes 66, 68. At least one and preferably both of the membranes 66, 68 are disposed in tension in the opening. The space between the membranes is expandable when filled with working fluid.

In one example, each membrane is no more than two mils (0.002") thick and more preferably is between one mil and two mils in thickness (0.001"-0.002"), inclusive. The example preferred membranes 66, 68 are co-extensive with the opening and like the opening are more or less square, with the length of top and bottom edges of the example membranes being approximately equal (within ±10% and more preferably within ±5%) of the lengths of the left and right edges of the membranes. Thus, the working fluid chamber between the membranes is also rectilinear and in the preferred embodiment no obstructions exist between the membranes, meaning the working fluid chamber is a complete rectilinear, more or less square chamber.

Owing to the thinness of the membranes 66, 68 and the closeness of the cold plates 30, 32 to each other and to the membrane assembly between them when the cassette is engaged with the cold plates, the system shown in the figures affords low impedance of heat transfer between the refrigerant circulating in the cold plates and the working fluid circulating between the membranes 66, 68. The working fluid chamber between the membranes inflates due to backpressure generated by working fluid flow, eliminating or reducing the need for a moving mechanism in the cold plates. Moreover, the narrow slot 34 between the two cold plates provides better heat transfer by reducing the conductive path length between the cold plates and the working fluid. The frame allows for ease of handling, such as insertion and removal of the cassette with/from the cold plates.

With respect to the example working fluid chamber between the membranes 66, 68 having a width-to-length aspect ratio near 1:1 (i.e., square or nearly so), the amount of backpressure required to induce working fluid flow through heat exchanger is reduced compared to a less square configuration. This reduces the amount of work that a working fluid pump must perform, which is desirable for two reasons. One, since the pump may be disposable, lower performance requirements translate into a lower cost disposable and quieter system. For instance, peristaltic roller pumps offer quiet operation and a low-cost disposable element, but operate most efficiently when only modest pressures are required. Two, lowering the working fluid pump work reduces the amount of heat transferred into the working fluid by the pump itself. Also, a low width/length aspect ratio results in slower working fluid velocity which reduces amount of mixing, but this otherwise desirable (from a heat exchange standpoint) effect is negligible in the present example system since the Reynolds numbers are typically <1000, suggesting a laminar flow regime. Furthermore, a low width/length aspect ratio significantly reduces the number of bends (or "corners") in the fluid flow path. These bends are areas of mixing for the fluid which promotes heat transfer. Without them, a fluid boundary layer builds up. However, this effect is offset herein by maintaining a narrow slot between the cold plates. This way the primary heat transfer mechanism is by conduction, but the conduction path length (and therefore boundary layer) is small, resulting in a relatively high rate of heat transfer.

In preferred examples, the membranes 66, 68 are stretched under tension during assembly to the frame. This tension can be maintained over the shelf life of the product. Pretensioning minimizes wrinkles in material, which is beneficial because wrinkles can impede working fluid flow and create air gaps which reduce heat transfer between the working fluid and cold plates. Wrinkles can also complicate insertion of the membrane assembly into the narrow slot 34.

To establish pre-tensioning of the membranes, the frame may be made in halves and posts such as threaded fasteners 70 (FIG. 5) can extend transversely to one half of the frame, with the membranes 66, 68 being stretched over the posts and holes made in the membranes to receive the posts. The other half of the frame is then positioned to sandwich a rectilinear border portion 74 (only the innermost portion of which is shown in FIG. 5) of the membrane assembly between the frame halves, and a closure such as respective nuts 72 engaged with the posts 70 to hold the frame halves together with the membrane assembly held in tension between the frame halves. FIG. 4 shows that the working fluid chamber is closed off at the bottom by a bottom seam 74A of the membrane assembly, which is part of the border portion 74.

In the border portion 74, at least one and preferably more layers of polymer film may be used to reinforce the membranes 66, 68 to establish welded seams through which (at the sides of the membrane assembly) the post holes are formed, allowing for easier fabrication. By placing reinforcing layers on the border portion 74 only, the central "window" of the membrane assembly consists only of a single thin layer membrane between the working fluid and one of the cold plates 30, 32 to minimize impeding heat transfer. A die-cut reinforcement layer may be used which reinforces the entire perimeter with one piece of material.

In some examples, the polymer membranes 66, 68 are highly stretchable, at least greater than 25% elongation. This allows the membranes to change from the empty flat state shown in FIGS. 4 and 5 to an inflated shape (within the slot 34 between the cold plates) without wrinkling. It also allows the membranes to easily conform to features on the faces of the cold plates.

Additionally, the membranes may be made of a material which can also be made into tubing. Tubes such as the inlet and outlet tubes 58, 62 shown in FIG. 4 can then be thermally welded (e.g., using RF sealing) to the membranes, which is more reliable and quicker than adhesive bonding. The membranes 66, 68 need not provide their own lateral support because the cold plates 32, 34 and frame provide the support for the inflated membrane assembly, allowing it to withstand the pressure generated as a result of working fluid flowing through between the membranes. Structural features may be located on the cold plates to optimize heat transfer. This can be economically advantageous because the cold plates are reusable components. Manifolds can be cut into the cold plates to even out the distribution of saline flow.

Figure 6:
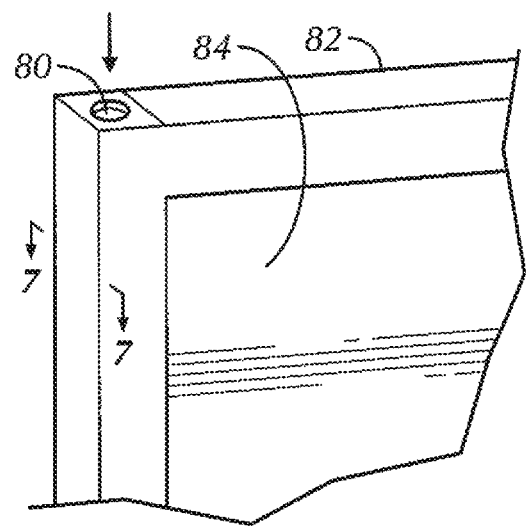
FIG. 6 is a perspective view of an alternate cassette in which the inlet and outlet tubes are formed in the frame of the cassette, with portions broken away for clarity.
Figure 7:
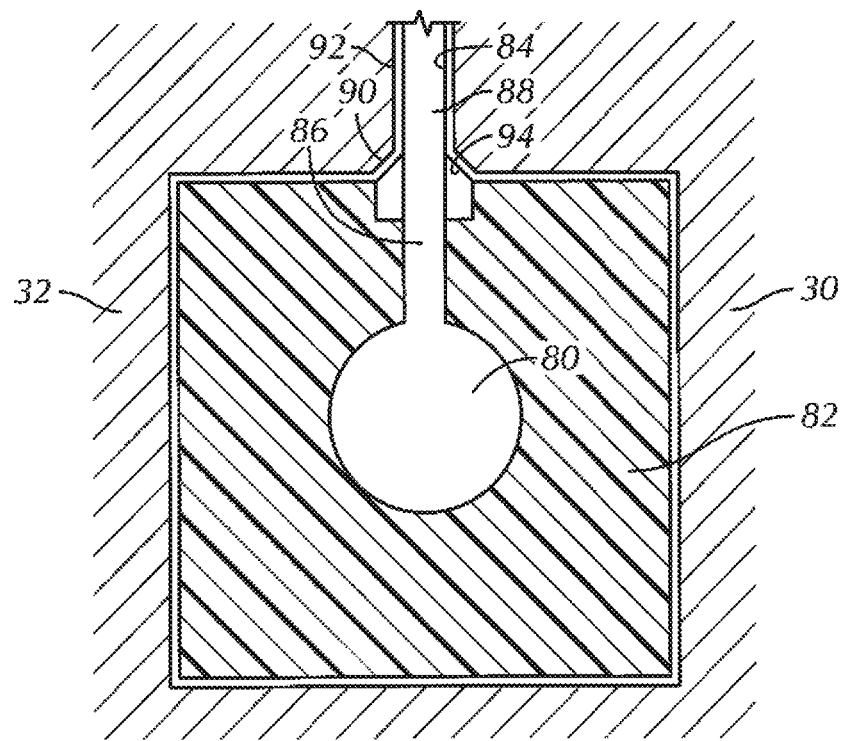
FIG. 7 is a view in partial cross-section as seen along the line 7-7 in FIG. 6, with portions broken away for clarity, and assuming the cassette is engaged between the cold plates.

FIGS. 6 and 7 show that alternatively, a working fluid inlet 80 may be formed in the left rail of a frame 82 holding a membrane assembly 84 in tension. It is to be understood that a working fluid outlet may be formed in the right rail of the frame 82. The inlet 80 and outlet may extend almost the entire length of the rail if desired or may extend only part way down the rail. In any case one or more lateral channels 86 extend from the inlet 80 to the working fluid chamber 88 of the membrane assembly 84 to establish fluid communication between the inlet (and outlet) of the frame 82 and the working fluid chamber. If desired, the cold plates 30, 32 may be formed with a chamfer 90 at the start of the slot 92 in which the membrane assembly 84 is disposed, with a complementarily shaped chamfer 94 being formed in the rail of the frame 82, to accommodate any "ballooning" of the membrane assembly 84 at the frame/membrane interface as the saline flows out of the frame into the membrane assembly.

Figure 8:
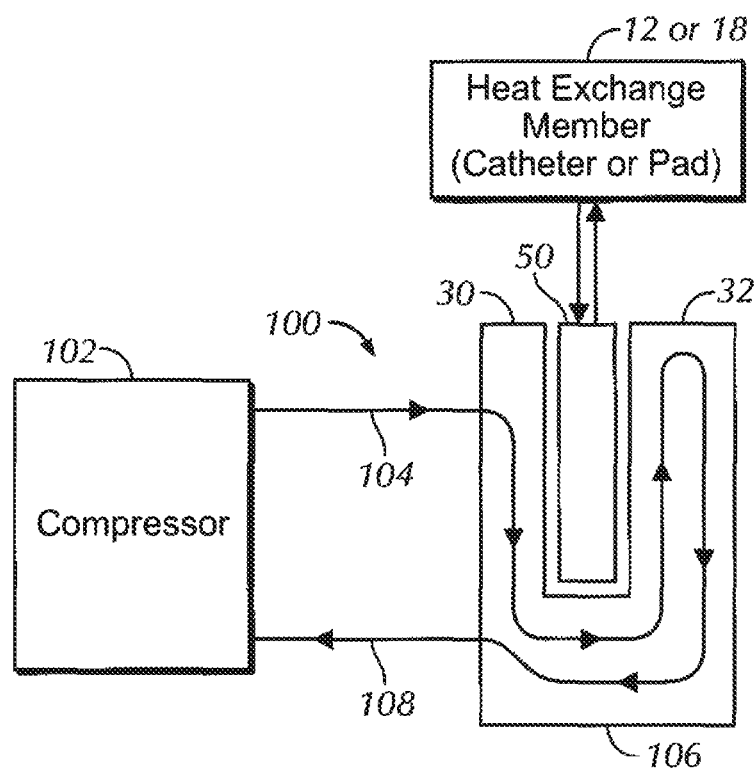
FIG. 8 is a schematic diagram of a refrigerant-working fluid system.

FIG. 8 shows an example system 100 that may use the fluid cassette 50 between the cold plates 30, 32. The system 100 may be an embodiment of either system 14, 20 shown in FIG. 1, for example. Refrigerant circulates from a compressor 102 through a refrigerant supply line 104 to at least one of the cold plates as shown. In the embodiment shown, the refrigerant circulates through a cold plate bottom coupler 106 from the first cold plate 30 to the second cold plate 32 and back to the compressor 102 through a refrigerant return line 108. In other embodiments the refrigerant may flow only through the first cold plate 30 which, owing to thermal coupling through the bottom coupler 106 with the second cold plate 32, equalizes the temperature of the second cold plate 32 with the temperature of the first cold plate 30. Yet again, separate refrigerant supply and return lines apart from the lines 104, 108 may be provided between the compressor 102 (or indeed a second compressor) and the second cold plate 32.

Thus, as shown in FIG. 8 only two fluid loops—refrigerant and working fluid—need be used. The "prime mover" of the heat exchange in the system 100 is the refrigerant loop with compressor, and it directly exchanges heat with the end use fluid system, the working fluid loop.

While the particular PATIENT HEAT EXCHANGE SYSTEM WITH TWO AND ONLY TWO FLUID LOOPS is herein shown and described in detail, the scope of the present invention is to be limited by nothing other than the appended claims.

What is claimed is:

1. A heat exchange system for exchanging heat with working fluid from an intravascular heat exchange catheter or an external heat exchange pad, comprising:
   a working fluid circuit configured for circulating working fluid between a cassette and the intravascular heat exchange catheter or the external heat exchange pad; and
   a refrigerant circuit configured for circulating refrigerant between a compressor and first and second heat exchange plates such that the refrigerant flows from the compressor to the first heat exchange plate and from the first heat exchange plate to the second heat exchange plate via a bottom coupler, and the refrigerant flows back to the compressor via the bottom coupler,
   wherein the first and second heat exchange plates define a cassette slot between the first and second heat exchange plates for receiving the cassette,
   wherein the refrigerant circuit including the first and second heat exchange plates is configured to directly exchange heat with the working fluid circuit so that the heat exchange system includes only two fluid loops.

2. The heat exchange system of claim 1, wherein the first and second heat exchange plates abut each other along side walls thereof, and wherein cassette frame receptacles are respectively vertically elongated and located immediately inboard of the side walls, the cassette slot extending between the side walls and terminating at the cassette frame receptacles, wherein the cassette frame receptacles are wider than the cassette slot and extend past opposed sides of the cassette slot.

3. The heat exchange system of claim 1, the first and second heat exchange plates are configured to support membranes of the cassette when the cassette is disposed between the first and second heat exchange plates.

4. The heat exchange system of claim 1, wherein the first or second heat exchange plate includes a fluid inlet and a fluid outlet connected by a pathway inside the first or second heat exchange plate, and wherein the pathway is configured to receive the refrigerant.

5. The heat exchange system of claim 4, wherein the pathway inside the first or second heat exchange plate is formed with a serpentine passageway.

6. The heat exchange system of claim 1, wherein a distance between the first and second heat exchange plates is between twenty nine millimeters and thirty one millimeters (0.029"-0.031").

7. The heat exchange system of claim 1, wherein the first or second heat exchange plates are square.

8. The heat exchange system of claim 1, wherein the cassette slot is on a first side of the first heat exchange plate, and wherein an inlet to the first or second heat exchange plate and an outlet from the first or second heat exchange plate are on a second side of the first heat exchange plate opposite the first side.

9. The heat exchange system of claim 1, wherein the first or second heat exchange plate is associated with its own respective refrigerant inlet and outlet tubes through which each heat exchange plate communicates with a source of the refrigerant.

10. The heat exchange system of claim 1, wherein at least one side wall of the first and second heat exchange plates defines a conduit configured to receive the refrigerant therethrough.

11. A system comprising:
    two heat exchange plates defining a slot between them configured for receiving a working fluid cassette through which working fluid flows to and from an intravascular catheter in a working fluid circuit wherein the two heat exchange plates communicate with a source of a refrigerant,
    wherein the two heat exchange plates abut each other along side walls thereof and respective cassette frame receptacles are vertically elongated and located immediately inboard of the side walls and are formed in each plate with the slot extending between the side walls,
    wherein the two heat exchange plates are a part of a refrigerant circuit configured to directly exchange heat with a working fluid circuit in a system with only two fluid loops, and
    wherein the two heat exchange plates include a bottom coupler or a channel through a side wall such that the refrigerant flows from a compressor to one of the two heat exchange plates and then to the other one of the two heat exchange plates through the bottom coupler or the channel through the side wall, and the refrigerant flows back to the compressor through the bottom coupler or the channel through the side wall.

12. The system of claim 11, wherein a distance between the two heat exchange plates is less than forty millimeters (0.040").

13. The system of claim 11, wherein a distance between two heat exchange plates is between twenty nine millimeters and thirty one millimeters (0.029"-0.031").

14. The system of claim 11, wherein at least one heat exchange plate of the two heat exchange plates is formed with a serpentine passageway through which the refrigerant flows.

15. The system of claim 11, wherein each heat exchange plate of the two heat exchange plates is associated with its own respective refrigerant inlet and outlet tubes through which each heat exchange plate communicates with the source of the refrigerant.

16. The system of claim 11, wherein the cassette frame receptacles are wider than the slot and extend laterally beyond opposed first and second edges of the slot.

17. The system of claim 11, wherein the heat exchange plates are thermally coupled, and wherein the refrigerant is configured to flow through a single heat exchange plate of the heat exchange plates to cool the heat exchange plates.

18. The system of claim 11, wherein the slot is on a first side of a heat exchange plate of the heat exchange plates, and wherein an inlet to the heat exchange plates and an outlet from the heat exchange plates are on a second side of the heat exchange plate opposite the first side.

* * * * *